United States Patent [19]
Canaani

[11] Patent Number: 5,882,880
[45] Date of Patent: Mar. 16, 1999

[54] HUMAN CHECKPOINT GENE AND GENE FOR ANTISENSE RNA THEREOF

[75] Inventor: Dan Canaani, Raanana, Israel

[73] Assignee: Ramot University Authority for Applied and Industrial Development Ltd., Ramat Aviv, Israel

[21] Appl. No.: 817,436

[22] PCT Filed: Oct. 11, 1995

[86] PCT No.: PCT/US95/12445

§ 371 Date: Jun. 11, 1997

§ 102(e) Date: Jun. 11, 1997

[87] PCT Pub. No.: WO96/11562

PCT Pub. Date: Apr. 25, 1996

[30] Foreign Application Priority Data

Oct. 11, 1994 [IL] Israel ........................................ 111238

[51] Int. Cl.[6] .......................... C07H 14/47; C07H 21/00; C12N 15/85; C12Q 1/02

[52] U.S. Cl. .......................... 435/29; 435/320.1; 530/350; 536/23.5

[58] Field of Search .................................. 435/6, 7.21, 29, 435/91.1, 91.4, 91.41, 91.42, 172.1, 172.3, 320.1, 325, 366; 514/44; 530/350; 536/23.5, 24.5; 935/78, 80

[56] References Cited

U.S. PATENT DOCUMENTS 5,585,479 12/1996 Hoke et al. .............................. 536/24.5

FOREIGN PATENT DOCUMENTS

93/23571 11/1993 WIPO .
96/11562 4/1996 WIPO .

OTHER PUBLICATIONS

Gewirtz et al. Facilitating olignucelotide delivery: Helping antisense deliver on its promise. Proc. Natl. Acad. Sci. USA 93: 3161–3163, Apr. 1996.
Zon et al. "Phosphorothioate oligonucleotides" in Oligonucleotides and Analogues: A Practical Approach, Eckstein, ed. IRL Press, New York, pp. 87–108, 1991.
Int'l Search Report (2 pages)—WO 96/11562.
Kuerbitz, Steven J., et al., "Wild–type p53 is a Cell Cycle Checkpoint Determinant Following Irradiation," Proc. Natl. Acad. Sci. USA, vol. 89, pp. 7491–7495, 1992.
Hillier, L., "The WashU–Merck EST Project" (unpublished).
Jeggo, P.A., et al., "Cloning Human DNA Repair Genes," Int. J. Radiat. Biol., vol. 66, No. 5, pp. 573–577, 1994.
Canaani, Dan et al., Immortalization of Xeroderma . . . Replication, Somatic Cell and Mol. Gen., vol. 12, No. 1, 1986, pp. 13–20.
Stark, Merav et al., Ultraviolet Light–Resistant . . . Repair–Proficient, Biochem. and Biophys. Res. Comm., vol. 162, No. 3, 1989, pp. 1351–1356.
Naiman, Tova et al., A Hypodiploid Karyotype . . . Complements, Cancer Genet Cytogenet 40:65–71, 1989, pp. 65–71.
Clarke, A.R. et al., Thymocyte Apoptosis Induced . . . Pathways, Nature, vol. 362, 1993, pp. 849–852.
Dulic, Vjekoslav et al., p53–Dependent Inhibition of Cyclin–Dependent . . . Arrest, Cell, vol. 76, 1994, pp. 1013–1023.
El–Deiry, Wafik S. et al., WAF–1, a Potential . . . Suppression, Cell, vol. 75, 1993, pp. 817–825.
Hartwell, Leland H. et al., Checkpoints: Controls . . . Events, Science, vol. 246, 1989, pp. 629–634.
Jacobson, Michael D. et al., Bcl–2 Blocks Apoptosis . . . DNA, Nature, vol. 361, 1993, pp. 365–369.
Lowe, Scott W. et al., p53 is Required for Radiation–Induced . . . Thymocytes, Nature, vol. 362, 1993 pp. 847–849.
Kastan, Michael B. et al., Participation of p53 . . . Damage, Cancer Res. 51, 1991, p–p. 6304–6311.
Pereira–Smith, Olivia M. et al., Genetic Analysis of . . . Groups, Proc. Natl. Acad. Sci. USA, vol. 85, 1988, pp. 6042–6046.
Takeda, Jun. et al., A Molecular Inventory of . . . Clones, Human Mol. Gen 2, 1993, pp. 1793–1798.
Teitz, Tal et al., Isolation by Polymerase Chain . . . Cells, Gene, vol. 87, 1990, pp. 295–298.
Teitz, Tal et al., Complementation of the UV–Sensitive . . . cDNA, Proc. Natl. Acad, Sci. USA, vol. 84, 1987, pp. 8801–8804.
Yonish–Rouach, Elisheva, Wild–Type p53 . . . Interleukin–6, Nature, vol. 352, 1991, pp. 345–347.

*Primary Examiner*—Nancy Degen
*Assistant Examiner*—Thomas G. Larson
*Attorney, Agent, or Firm*—Blank Rome Comisky & McCauley LLP

[57] ABSTRACT

A novel human radiation protecting checkpoint (RAP-1) gene and the RAP-1 protein encoded by the gene are disclosed. RAP-1 is believed to be involved in the regulation of cell cycle progression and/or programmed cell death (apoptosis). A human antisense RNA which can bind to the mRNA of the human RAP-1 protein, as well as the DNA from which the antisense RNA is transcribed are also disclosed. Additionally, a method for isolating DNA damage-monitoring checkpoint genes is described. The use of the DNA and RNA sequences and of the protein of the invention for the eary detection, prevention and/or treatment of cancer, AIDS and other diseases is also discussed.

13 Claims, 8 Drawing Sheets

```
   1 TCCAGCGGGGGCAACGGGGGGGGCAGCGGGGGGGCAGCGGGCGGGGGCAGCGGGGGGCTACTGTCTGGGCTGAGCAGTAGTGCC
  69 TCTCGGGTGGCGGGTTTCTAGGCTGCAGGGGCTTGGTAGGTGGTGGCAAGGGGGCGGGCGGTCGGTCGGGGGCCCTGCATG
 137 GGAAGAGTGCCCGCCCGCTTGGCGGCCCCTGGCATGAGAGATGAGCGCTCCGGTTCTGCCGCGGGGAACATTGTTAAT
 205 CGTCCCCAGCCAGTGCCGCCACCCCGGCCCGGCCTGCCTGGCGTCTTCGACATCTTGGAACATTGTGCCGGAACATTGTTAAT
 273 TGGAGCTGCGTCTCAGCAGCGGGTCTTGATACCTTGATACCTACTTCACTTGTGTACTACTGAAAAGATATAGA
 341 AGAAATGGCCATCAGTCCTTGATACCTTAAGAATTCCTGAATCCCACGTGGCGAAGTCTCGATTTTGGAA
 409 AGAATTTATAGAAgtgagGTGATTAAGAATCCTGTGTCTTGTTCTTGTGATGGGCTGAAATACTTGGGTCAGCAGATTCA
 477 TTATGCCAGACCGTCTTGATTGAATGGAAAGTCTGTTTGGGCTGAAATACTTGGGTCAGCAGATTCA
 545 ATCTACCAGCTGTTGATTGAATGAGAGATAATTTGGGCTGAATGATGGATCAGAACTATATGGTGTCCATTGAACATA
 613 TGCCCGAAACCAAAATGCTCAGAAGACTATTCTCTGCAGGTGGATCAGAACTGTGTTGTTCAATTCTTAC
 681 AGGGTATTCAAATGCTCAGAAGACTATTCTCTGCAGGTGGATCAGAACTGTGTTGTTCAATTCTTAC
 749 GATGTCTTCTTTTGCTACGGCTTCATAGAGCCCAGTGTGCAATTAAACAGACTCAGTAACTGTTCA
 817 GAAAATTGGAAAGGAAATTGAAGAAAACTAAGACTCACATCTACACAAGCAATGAACTGAAAAAAAAAAA
 885 GTGAATGCTGCAGTTAAAATTTGGTGCTTCAGAATGAACTGGCAGAAGCAAGGAAGTTTGGGA
 953 CGGGAGGTGGCATTACTGCATAAGCAACAAATTGCATTACAAGACAAAGGAAGTGCATTTCAGCTGA
1021 GCACTCAAACTTCAACTTCAGAGGAATCCTCAGTTGACAATTCGTTGCAGGCAGTACTCTCTGAGCTTCCTAC
1089 AACTCTTTGAAGACTAATGCTCAGTTGACAATTCGTTGCAGGCAGTACTCTCTGAGCTTCCTAC
1157 ATTACCTATTGATTTGAATGAACATAAGGATTACTTGTATGCGGTGTCAAGTTGCACATCTGGTCTCCA
1225 GGACTTCCAAGCAAAGATGATGGAAGCATTGCCCCTGGTTATACTGCACATCTGGTCTCCA
1293 TGATTCCTTTTCCTACAAGTGCCCTCAGATATCCTATAATTCATAAGGGGTCTAGATCAACAATC
1361 AAAGACAATATCAATGACAAACTGACAGAAAAGGAGAGAGAGTTCCACTGTATCCAAAAGGAGGGA
1429 GAAGTTGCAGTTTGATTATGGTCTATCTTTGAACAAAAATATAGCACAGCTAAGATATCAACATG
1497 GACTAGGGACTTCCAGACTTGCCAACCCTCCAGTCCCAAACCCTTCCAGTGCAATCCCTGTTCCACCAGACATCCTTCATGGAGCATGGACTAATG
1565 GTCAGGTGTGACAGACATCACACTTCTGGGGGATCCCTCACCAGACATCCTTCATGGAGCATGGACTAATTGG
1633 GGGTGCAGATGTAGGCTTCTCTGGGGGATCCCTCACCAGACATCCTTCATGGAGCATGGACTAATTGG
1701 CTGAGAATGAGAGACTTCAGTAGAGACTTCAGTACAACTTACAACTTCCCAGTTACAACTTACAACTTCAGCATTAGCCTGTG
```

FIG. 3A

```
1769 ACCACCGTCCCTCCATGGGAGAGACCGAGAGAAAGATAACATCTCTATCCTCTCCTTGGATACTC
1837 CTTGGACTTCTCCAAAGAAAACAAGAACAAGGAGAGGAGGATCTAGTTGGCAGCTTAAACGGAGGCCACG
1905 CGAATGTGCACCTAGCCAAGAACAAGGAGAAGCCCTCCGGGCACGGCCACAGTCAATGGCACT
1973 CTCCTACCCAGCGAGCAGGCGGGTCCGCAGTGTCGCCAGTTCCAGGCGAGTTCCACCAGTCTCAGA
2041 AGCTGAGTCTGTCTGTAGAAGCTAGAAGCATTTAACTGCATCCCAGTGGACAGTGCTGTGGCAGTAGAGTGTGACGAAC
2109 AGGTGATCAGCTAGAAGCATTTAACTGCATCCCAGTGGACAGTGCTGTGGCAGTAGAGTGTGACGAAC
2177 AAGTTCTGGGAGAGAATTTGAAGAGTGTCCGATAAGTGAAGTGAGCAGGTCAACAGTAGGACTGGGCAGAAgCTCT
2245 CGCCGGCGGCGCAGGAGTTCCGATAAGTGAAGTGAGCAGGTCAACAGTAGGACTGGGCAGAAgCTCT
2313 GCCTAAAATGAAGTGAAAGTGCACTTAACCCTTTGTGATAATGATGACACAAATGAATATTAATGG
2381 AGGATATTCCTCGGAAAAAACAGACTTTGGAATGAAGGAGGACTCAGGATCATTGTTATCAGTGGGC
2449 CAAAGTTAGATTTTGCTTTCAAGATTTGCTTTCGAGTCACCTTTAGCTATTTGTCTGCTTTTATTTACCCTTGTATGT
2517 AGTTGAAAGAGCTTACAGCTCGAGTCACCTTTAGCTATTTGTCTGCTTTTATTTACCCTTGTATGT
2585 TATCCTCAGAGGGAAGATGATAATATATATAAATGAACACACCTTAGTTCTCATAANCATT
2653 TGCCCTCACCATGGTTTATAAAACTTTGGGAAAACGGAATATTCAGAAATAGGTTCCGCCATGTACT
2721 GAAAGGTCTGTGTGGCCATCTGTGTGAGGTAGATGAAGAAGCAGCATAGTGGTCTCCTTACATCTAGGCTA
2729 ACTGTCCCTCTTCCTGCCCCCGGGTACCACAGTTCACCTTAGACGTTCACTGGTTCTGTAACCCAGTAGCTGTG
2857 GTGGATGGGCATGGTTCCTGAAAACAGGACATCAAGATTCACTGGTTCTGTAACCCAGTAGCTGTG
2925 ACGTTCCATCTCTTCTAACCAGCCATGGCCTTCCCCTGGATCCAAGGACCTTGGGCAGATGCTGTGGTCAGAACTAGGCAT
2993 TTAGATGAAAAACTGCTCTGTGGGGGCAAGTTTTATGTGGGCAGATGCTGTGGTCAGAACTAGGCAT
3061 ATGCCATCCATCTCTTCTAACCAGCCATGGCCTTCCCCTGGATCCAAGGACCTTGAGGTTACTGCAGTCAG
3129 GCTTTCTGGCAATGCACTCACCAGACAGACAAAAATCCTTGATGTAAATCCATGTAATTATTAAATTTA
3197 GTCAGAAGGTCAGCATTTACATGACAGAATGTATGTAGAGAGACATAGAATACTATTGGTGATGTGTGCAAACTGCA
3265 AGGCAGTCAGATAGTGGATTAAGAGGCTAGACGAGAGACATAGAATACTATTGGTGATGTGTGCAATT
3333 TCATGAATATTAAATTATGTTTCGAAGTCACATTGCCTCAGGGTTGCATTCCCGCATTCAGATTTCATTGTGCTGATGA
3401 CTTTATACGTTACGTACCCAAGGACATTGCCTCAGGGTTGCAAACTCTTTAAAGGCAAATTTATCCA
3469 TATATCCATGTATTATTATAGAATAAAAATTGAAGTTACTTC
```

FIG. 3B

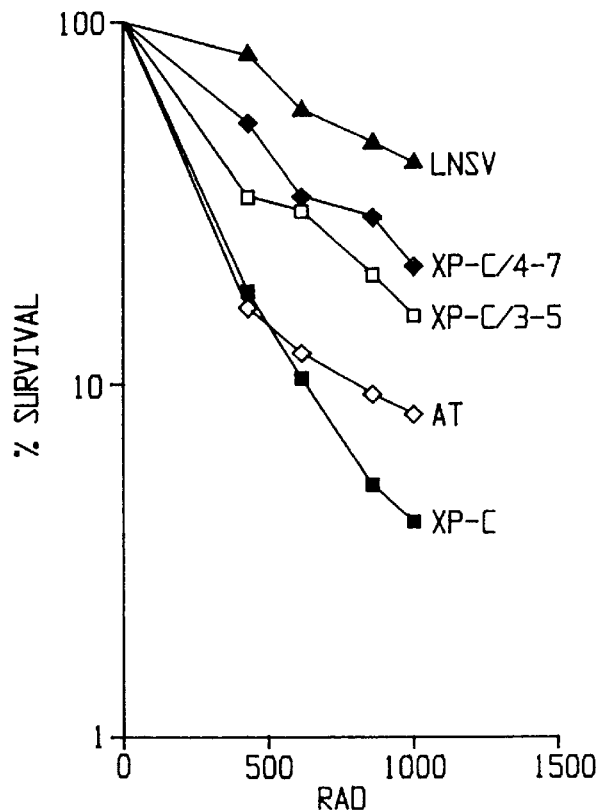
FIG. 5
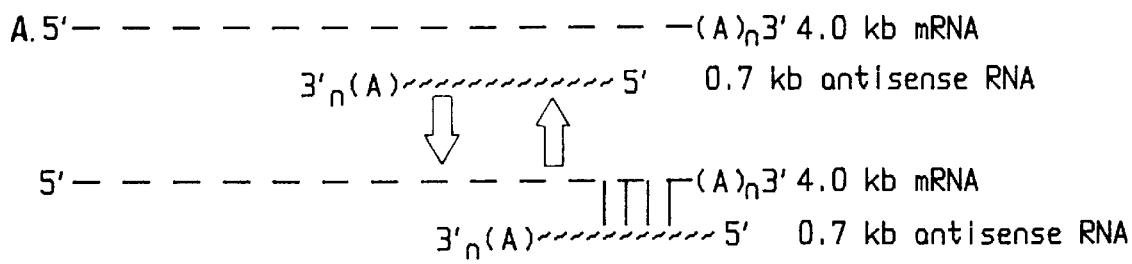
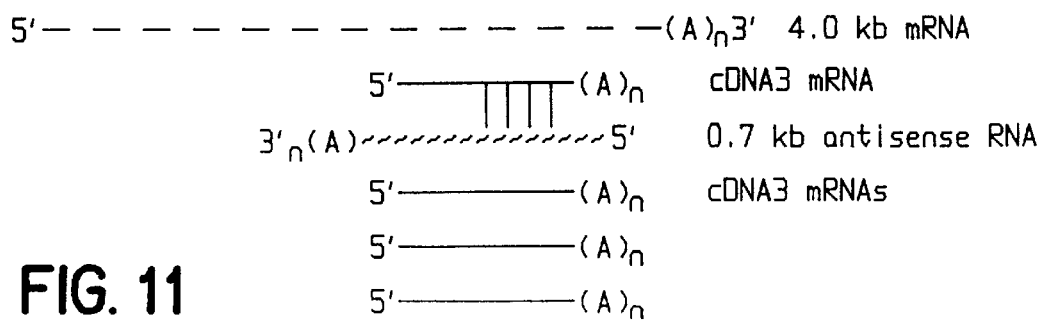
FIG. 11

```
  1 MSASASVGGP VPQPPPGPAA ALPPGSAARA LHVELPSQQR RLRHLRNIAA
 51 RNIVNRNGHQ LLDTYFTLHL CSTEKIYKEF YRSEVIKNSL NPTWRSLDFG
101 IMPDRLDTSV SCFVVKIWGG KENIYQLLIE WKVCLDGLKY LGQQIHARNQ
151 NEIIFGLNDG YYGAPFEHKG YSNAQKTILL QVDQNCVRNS YDVFSLLRLH
201 RAQCAIKQTQ VTVQKIGKEI EEKLRLTSTS NELKKKSECL QLKILVLQNE
251 LERQKKALGR EVALLHKQQI ALQDKGSAFS AEHLKLQLQK ESLNELRKEC
301 TAKRELFLKT NAQLTIRCRQ LLSELSYIYP IDLNEHKDYF VCGVKLPNSE
351 DFQAKDDGSI AVALGYTAHL VSMISFFLQV PLRYPIIHKG SRSTIKDNIN
401 DKLTEKEREF PLYPKGGEKL QFDYGVYLLN KNIAQLRYQH GLGTPDLRQT
451 LPNLKNFMEH GLMVRCDRHH TSSAIPVPKR QSSIFGGADV GFSGGIPSPD
501 KGHRKRASSE NERLQYKTPP PSYNSALAQP VTTVPSMGET ERKITSLSSS
551 LDTSLDFSKE NKKKGEDLVG SLNGGHANVH PSQEQGEALS GHRATVNGTL
601 LPSEQAGSAS VQLPGEFHPV SEAELCCTVE QAEEIIGLEA QVSPQVIS
```

FIG. 6

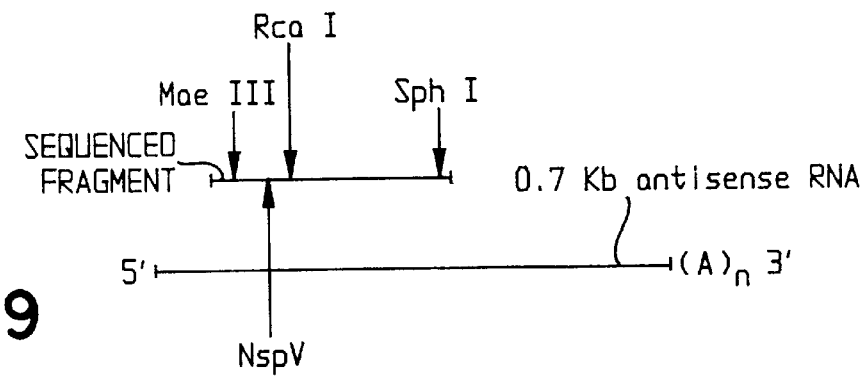

```
  1 CCCTGAGGCA AGTCTGGGTA CGTAACGTAT AAAGCAACAG CAAATGAAAT
 51 CTGAATGCGG GAATGACAAC TGGACTTCGA AACATAATTT AATATTCATG
101 AAATTGCACA CATACCAATA GTATTCTATG TCTCGTCTAG CCTCTTAATC
151 CAACTATCTC AACTGCCTTG CAGTTTGCCT ACCAGACACC CCAACTCTCT
201 ACATACATTC TGTCATGTAA ATGCTGACCT TCTGACTGAA ATTTAATAAA
251 TTAACATGGG ATTTACATCA AGGGATTTTT GTCTGGTGAG TGCATTGCCA
301 GAAAGCATGC CTAGTTCCTG AC
```

5,882,880

HUMAN CHECKPOINT GENE AND GENE FOR ANTISENSE RNA THEREOF

This application is a national phase filing under 35 U.S.C. §371 of application PCT/US95/12445 filed Oct. 11, 1995.

FIELD OF THE INVENTION

The present invention relates to genes and polynucleotides which regulate the cell cycle and/or programmed cell death processes (apoptosis), and in particular to checkpoint genes and proteins, related polynucleotides and a method for isolating these genes.

BACKGROUND OF THE INVENTION

Cancer cells typically display abnormal genomes with aneuploidy and chromosomal rearrangements, including high frequency gene amplification at late stages of tumor progression. The existence of a number of human cancer prone genetic diseases with defects in DNA repair, whose non-tumorous cells display unstable karyotypes provides strong evidence that genomic instability is heritable, and associated with a predisposition to cancer.

The development of a malignant cell is a multistep process. The spontaneous rate of mutation in normal somatic cells is less than $10^{-5}$ mutation/gene/generation. Thus, the accumulation of a number of genetic changes by a clone of cells would be more likely to occur if an early step produces a genetically unstable cell. Eukaryotes have generated a variety of mechanisms for limiting the formation of abnormal, heritable genetic changes. These include mechanisms for maintaining fidelity of DNA replication and segregation, mechanisms for DNA repair, and checkpoint genes for cell cycle progression or for programmed cell death (apoptosis).

It has been assumed that one mechanism leading to genomic instability could be a defect in a DNA repair pathway. The recent findings of a defective mismatch repair in hereditary non-polyposis colorectal cancer confirmed that assumption.

Another possible mechanism for generating genomic instability is perturbation of the normal cell cycle control. At least two stages in the cell cycle are regulated in response to DNA damage—the $G_1$-S and the $G_2$-M phase transitions. These transition serve as checkpoints at which cells delay cell cycle progression, presumably to allow repair of damage before the cell enters either replicative DNA synthesis ($G_1$-S), when damage could be perpetuated, or before the cell enters mitosis ($G_2$-M), when chromosomal breaks would result in the loss of genetic material.

This possibility was initially supported by features of Barrett's esophagus, a cancer-prone syndrome, which shows a sequential appearance of high S and/or high $G_2$ phase populations, followed by the emergence of aneuploid cells and subsequently the development of tumors. The demonstration by Weinert and Hartwell that mutations in the yeast radiation-monitoring $G_2$-M checkpoint gene RAD9 (Hartwell and Weinert, 1989) and in the $G_1$-S checkpoint genes RAD5 and RAD51 lead to increased spontaneous chromosome loss further supported this supposition. These observations led Hartwell to propose that some of the tumor suppressor genes actually operate as cell cycle checkpoint genes. The prediction was soon proven correct when Kastan and colleagues demonstrated that human p53 is a $G_1$-S checkpoint gene which prevents entry into S phase when DNA is damaged by irradiation (Kastan et al., 1991; Kuerbitz et al., 1992). This result becomes more noteworthy when we take into account that the loss or mutation of the p53 gene is the most common alteration found in sporadic, non familial cancers of either solid tumor or hematopoietic ones. Furthermore, p53 also protects the cell from genomic instability reflected in gene amplification and acts as a checkpoint by activating an inhibitor (p21) of $G_1$-S phase transition (El-Deiry et. al., 1993; Dulic et. al., 1994).

Another example of the involvement of aberrations in cell cycle control with human cancers is the recognition that an inhibitor (p16) of cyclin-dependent kinase 4 is encoded by a tumor suppressor gene, which is defective in various human cancers including melanoma.

A further demonstration of the link between human cancers and the cell cycle machinery has been the finding that an oncogene involved in parathyroid adenoma (PRAD1) and B-cell lymphoma (bcl-1) actually encodes cyclin D1. Moreover, the cellular proteins sequestered by pRb include, in addition to the E2F transcription factor, cyclin D1 and perhaps cyclin D3. Phosphorylation of pRb by cdk2/cyclin E releases the cyclins D1/D3 from the complex, allowing them to associate with cdk(s) and phosphorylate "S-phase targets".

More recently it was shown that the fission yeast DNA damage monitoring G2 checkpoint genes rad24 and rad25 encode 14-3-3-protein homologs which associate with the oncogenic middle tumor antigen of murine polyoma virus.

Thus, the relationship between human cell-cycle checkpoint genes and human cancers has been firmly established. The role of p53 in DNA damaged-induced G1 arrest has resulted in this gene being considered as "the guardian of the genome". Seemingly this role of p53 in preventing mutations and chromosomal rearrangements or loss could have been sufficient to explain its tumor suppressor activity and its deletion/disregulation in over half of human cancers. However, over the past few years, another important function of p53 has been discovered and this is its requirement for apoptosis induced by radiation (UV as well as γ-rays), anti-neoplastic DNA damaging agents, oncogenes activation and withdrawal of hematopoietic survival factors (Yonish-Rouach et. al., 1991; Clarke et. al., 1993; Lowe et. al., 1993).

Thus p53 acts as a tumor suppressor gene by either causing a cell cycle arrest or by the induction of apoptosis. The mode of action of p53 at this "decision fork" depends on multiple factors which constitute the cellular milieu. Notable effectors are the tumor suppressor gene Rb which acts as a $G_1$ cell cycle checkpoint gene (repressor for S phase entry) as well as an anti-apoptotic gene whose disregulation is countered by p53 mediated apoptosis. Likewise it appears that the adenovirus E1A and c-myc onco-proteins sensitize cells deprived of growth factors to undergo apoptosis through sequestering of the pRb anti-apoptotic protein.

Another effector which counters apoptosis is the Bcl-2 proto-oncogene. Bcl-2 like p53 responds to growth factor withdrawal, DNA damage and oncogene activated apoptosis.

The classical dogma that antineoplastic agents cure cancer by selectively killing rapidly diving cells has proved to be incorrect. As outlined above, some oncogenes which induce entry into the cell cycle do in fact predispose cells undergoing untimely proliferation (for example under conditions of limited growth factor supply) to programmed cell death. Thus, due to varying apoptosis thresholds, radiation/chemotherapy may induce apoptosis in the tumor cell and merely a cell cycle arrest in the surrounding normal cells. Accordingly the success of tumor eradication by antineoplastic agents is critically dependent on the cellular balance between apoptotic and anti-apoptotic processes. One of the promising approaches to lower the threshold for radiation/chemotherapy-induced apoptosis would be to ablate the activity of anti-apoptotic gene(s) in the tumor, thereby curing the malignancy.

Few examples of natural antisense RNAs have been published. It is noteworthy, however, that natural antisense RNAs must have been conserved during evolution, and that the few mammalian examples known so far involve genes such as p53 and myc whose expression is essential for growth control.

SUMMARY OF THE INVENTION

It is an object of the present invention to provide a novel human radiation protecting checkpoint (RAP-1) protein and the DNA encoding it.

It is a further object of the present invention to provide a human antisense RNA which can bind to the mRNA of the human RAP-1 protein, as well as the DNA from which the antisense RNA is transcribed.

Additionally, it is an object of the present invention to provide a method for isolating DNA damage-monitoring checkpoint genes.

According to one aspect of the present invention, there is provided a gene encoding a radiation-protecting human checkpoint (RAP-1) protein. RAP-1 is believed to be involved in the regulation of cell cycle progression and/or programmed cell death.

Further in accordance with this aspect of the present invention, there is provided a DNA sequence selected from the group consisting of:
(i) a DNA sequence encoding a RAP-1 protein and having the nucleic acid sequence shown in FIG. 3 below (SEQ ID NO: 1);
(ii) a DNA sequence having the sequence of (i) in which one or more DNA codons has been added, deleted or substituted without significantly affecting the RAP-1 activity of the polypeptide encoded thereby;
(iii) a DNA sequence which is degenerate to the DNA sequence defined in (i) or (ii) as a result of the genetic code; and
(iv) a DNA sequence capable of hybridization to the DNA sequence of (i), (ii) or (iii) under moderately stringent conditions.

RAP-1 activity is defined as any biological activity of the natural RAP-1 protein, including its regulatory activities in the processes of cell cycle progression and programmed cell death. A DNA sequence according to (ii) above would encode a polypeptide having at least 50%, preferably at least 70%, and most preferably at least 80% of the biological activity of the natural protein.

Moderately stringent conditions under (iv) above are defined as hybridization at 50° C. using 2×SSC buffer.

Also provided by the invention is a polypeptide comprising the amino acid sequence encoded for by the DNA sequence of the invention. In a preferred embodiment, the polypeptide comprises the amino acid sequence of FIG. 6 (SEQ ID NO: 2).

According to another aspect of the present invention, there is provided a gene capable of being transcribed into an antisense RNA to the mRNA of the RAP-1 protein.

Further in accordance with this aspect of the invention there is provided a DNA sequence capable of being transcribed into an antisense RNA to all or part of the mRNA transcribed from the DNA sequence of the invention. In a preferred embodiment the DNA sequence comprises the nucleic acid sequence of FIG. 10 (SEQ ID NO: 3).

Also provided is an RNA sequence comprising an antisense RNA to the mRNA of a RAP-1 protein. The natural antisense RNA or the corresponding antisense oligodeoxyribonucleotides could be used to stimulate radiation/chemotherapy induced apoptosis of the treated tissue.

According to yet another aspect of the present invention, there is provided a method for the isolation of DNA damage-monitoring checkpoint genes comprising the steps of:
(i) transfecting normal cells with an antisense cDNA library;
(ii) γ-irradiating said transfected cells;
(iii) identifying radiation-sensitive colonies; and
(iv) recovering plasmids from said colonies which comprise DNA damage-monitoring checkpoint genes.

The practical importance of human checkpoint genes in general and the genes of the invention in particular is that they can be used as markers for early detection and prevention of tumor progression. The same genes or others of the checkpoint class may also be used to increase the efficiency of various types of cancer treatments, by facilitating the design of new drugs which enhance the antineoplastic effects of the treatments. This can be achieved through enhancement of DNA damage-induced apoptosis of the treated tissue by one or more of the following: (1) RAP-1 dominant negative mutants (in the form of DNA, RNA or protein); (2) RAP-1 antisense RNA gene, RNA, or synthetic oligodeoxyribonucleotides thereof; and (3) small molecules which can disrupt the activity of the RAP-1 protein or enhance the RAP-1 antisense RNA level.

Furthermore, the RAP-1 gene, its putative suppressor antisense RNA gene or other checkpoint genes recovered through use of the general method of the invention may be disregulated in other pathogenic conditions besides cancer, such as autoimmune diseases, neurodegenerative disorders, osteoporosis, hematopoietic diseases and viral infections (including AIDS), etc. For example, defects in the expression of the RAP-1 antisense RNA or enhancement of RAP-1 activity could be involved in the failure of the immune system to remove autoimmune cells in diseases such as autoimmune diabetes mellitus, psoriasis, SLE or rheumatoid arthritis. Alternatively, defects in RAP-1 gene expression or elevated production of RAP-1 antisense RNA could lead to increased cell death associated with such diseases as Alzheimer, Parkinson, ataxia telengiectasia, osteoporosis, several hematopoietic diseases and AIDS. Thus, the DNA and RNA sequences of the invention can be used to prevent and/or treat these diseases.

The antisense RNA of the invention may also be used as a general effector in gene therapy, by modulating the activity of genes engineered to be fused to the RAP-1 3'UTR tag and delivered into human cells/tissues by gene therapy protocols.

BRIEF DESCRIPTION OF THE DRAWINGS

The present invention will be better understood from the following detailed description of preferred embodiments, taken in conjunction with the following drawings in which:

FIGS. 3A and 3B show the cDNA sequence encoding RAP-1 (SEQ ID NO: 1). The cDNA3 sequence corresponds to nucleotides 3107 to 3509;

FIG. 5 illustrates γ-ray survival of SV40-transformed human fibroblasts. XP-C is the GM2096-SV3 cell line, XP-C/3-5 and XP-C/4-7 are transfectants derived from it by introduction of rescued PCR products nos. 3 and 4, respectively. AT is an SV40-transformed ataxia telangiectesia cell line, and LNSV is an SV40 immortalized Lesch-Nyhan syndrome derived cell line;

FIG. 6 shows the amino acid sequence of RAP-1 (SEQ ID NO:2). The sequence corresponds to nucleotides 176-2119 of the sequence of FIG. 3 (SEQ ID NO:1);

FIG. 9 is a partial physical map of the 0.7 kb cDNA for the antisense RNA, with the location of the sequenced fragment of FIG. 10 indicated;

FIG. 10 illustrates the cDNA sequence (SEQ ID NO: 3) of a fragment of the 0.7 kb cDNA of FIG. 9; and FIGS. 11A and 11B illustrate a proposed mechanism of action for cDNA3:

A. In nontransfected human cells, formation of the RNA duplex 4.0 kb mRNA-0.7 kb RNA represses expression of the 4.0 kb mRNA;

B. Transduction and expression of cDNA3 releases the 4.0 kb mRNA from the duplex leading to its increased expression. A new duplex is formed between cDNA3 mRNA-0.7 kb antisense RNA.

DETAILED DESCRIPTION OF PREFERRED EMBODIMENTS

I. Checkpoint gene

It was originally intended to clone and characterize the human DNA repair gene that is defective in xeroderma pigmentosum group C (XP-C) patients. The experimental approach was to complement the marked UV sensitivity (which stems from the defect in nucleotide excision DNA repair) by gene transfer, followed by rescue of the correcting normal human gene. For this purpose, we initially immortalized a primary xeroderma pigmentosum cell line GM2096 (XP1MI) belonging to a patient assigned to complementation group C. A simian virus 40 (SV40) DNA fragment, encompassing the whole early region (encoding for T antigen) and having a defective origin of DNA replication, had been used to transform the human fibroblast cell line mentioned above. Two independent XP-C transfectants acquired an indefinite lifespan in culture, while maintaining their UV sensitivity (Canaani et. al., 1986). Unlike most SV40-transformed human fibroblasts, the two established XP-C cell lines GM2096-SV3 and GM2096-SV9 possessed an identical hypodiploid karyotype of 44,XX,-19-,Xq+,-22, 15p + (Canaani et. al., 1986; Naiman and Canaani, 1989). Using the GM2096-SV3 cell line as a recipient, an expressible human cDNA library was transfected into it while selecting for acquisition of UV resistance.

Figure 1:
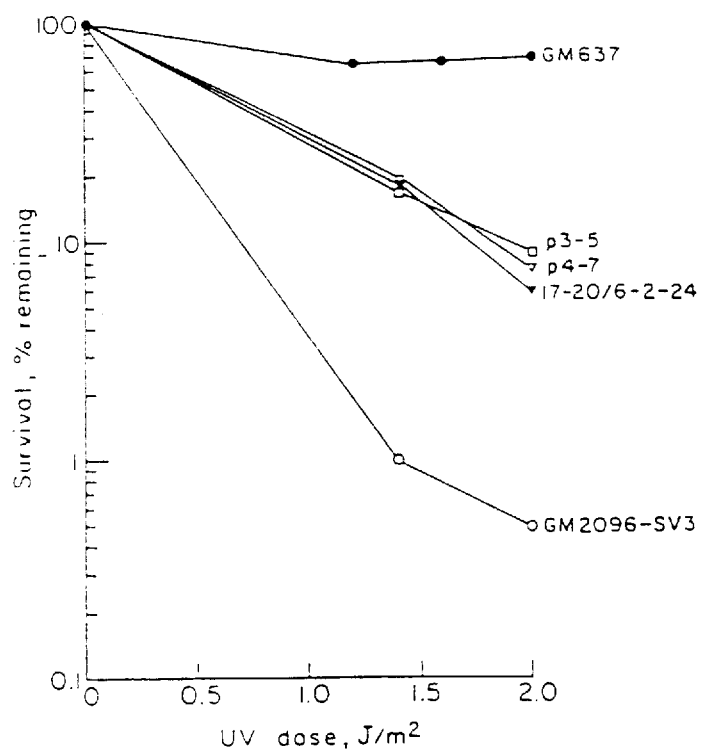
FIG. 1 illustrates the UV survival of SV40-transformed human fibroblasts. GM637 is an SV40-transformed normal fibroblast cell line, and GM2096-SV3 is an SV40-transformed XP-C cell line. Transfectants of the latter are: 17-20/6-2/24—secondary transformant, p3-5 and p4-7, which are transfectants derived by introduction of PCR products no. 3 and no. 4, respectively.

This treatment led to stable complementation to wild-type levels of both the UV-sensitivity and the excision repair deficiency in primary transformants (Teitz et. al., 1987; Stark et. al., 1989). Secondary transformants displaying a stable partial $UV^R$ phenotype were generated by transfection with a partial digest of total chromosomal DNA from one of the stable transformants (17-20/6) while selecting for expression of the "iendogenous" neo genes (Teitz et. al., 1987). Transfected cDNAs were rescued from the cellular DNA of a secondary transformant by their in vitro amplification using expression vector specific oligodeoxyribonucleotides as primers in a PCR reaction. Their expression in XP-C cells identified two PCR products (FIG. 1, nos. 3 & 4) which complemented the UV sensitivity of the recipient cell line to the same partial UV resistance levels exhibited by the secondary transformant from which the cDNA was rescued (Teitz et. al., 1990). Determination of the nucleotide sequences of these two PCR products has shown that they represent the same cDNA, which was named "cDNA3". PCR product no. 4 has an extension of about 100 bp of vector sequences on the 3' end, due to a weak secondary annealing site for PCR primer 1.

Figure 2:
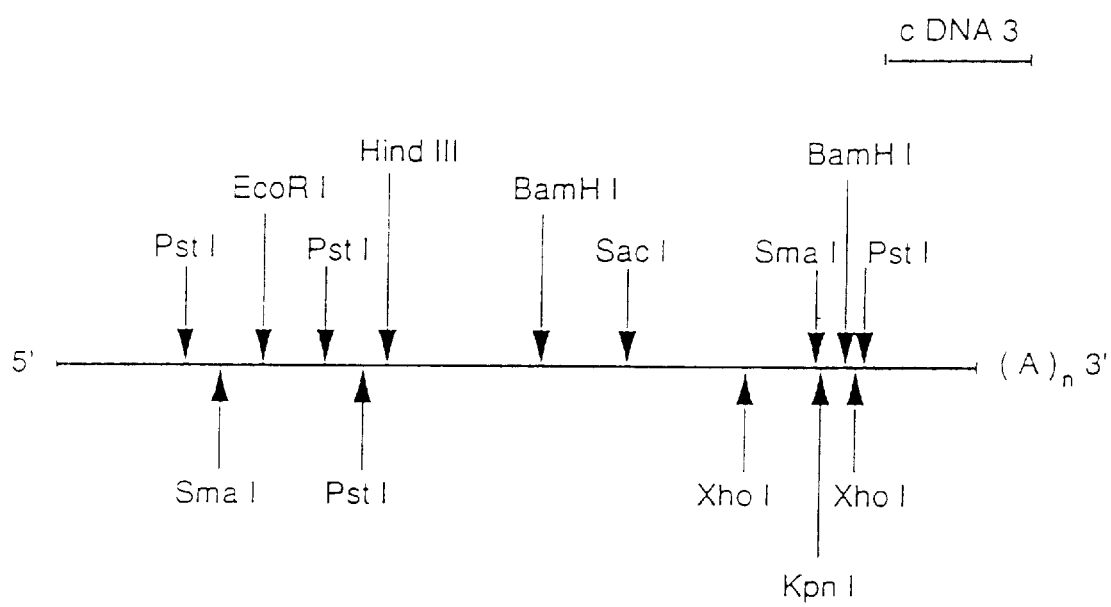
FIG. 2 is a physical map of the cDNA for the 4.0 kb RAP-1 mRNA, with restriction sites and cDNA3 sequence indicated.
Figure 4:
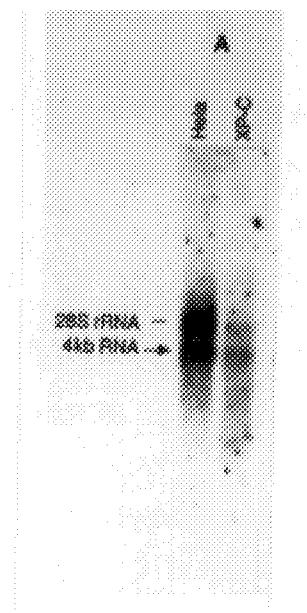
FIG. 4 is a Northern blot characterizing the RAP-1 mRNA. Hybridization of cDNA3-antisense riboprobe to Northern blots of total RNA extracted from Hela and SV40-transformed XP-C cells.

DNA sequencing (FIGS. 2 and 3) has shown that cDNA3 contains an insert of 482 bp, including a poly(dA) tail, but no initiation codon for translation. Northern analysis determined that cDNA3 represents a partial-length mRNA, as the normal human mRNA is 4.0 kb long (FIG. 4). Screening of a λgt10-K562 human cDNA library with cDNA3 as a probe led to the recovery of several cDNAs which extend up to 2.5 kb from the poly(A) tail. DNA sequence analysis of several of these clones has shown that they represent previously unpublished human DNA sequences, and that at least the first 1500 bp on the 3' end of the 4.0 kb mRNA constitute a noncoding region. Extensive analysis by Southern, Northern and RT-PCR (cDNA3 region only) derived samples from 12 XP-C families did not reveal any functional defects in that gene. In three independent experiments, expression of cDNA3 conferred only partial UV resistance upon the particular XP-C cell line which we previously immortalized (Canaani et. al., 1986). It therefore seemed unlikely that cDNA3 was by itself responsible for the full UV resistance displayed by its parent primary transformant. Moreover, among the primary transformants, cDNA3 copies were present only in the primary transformant 17-20/6 from which the partially UV resistant secondaries were derived. We have also shown that in contrast to the situation in primary transformants, the secondary transformants did not acquire the capability of UV-induced thymidine incorporation or DNA repair synthesis. It was therefore concluded that cDNA3 does not represent the gene which is defective in XP-C patients.

Since the possibility that cDNA3 expression directly affects DNA repair was ruled out, the hypothesis was raised that cDNA3 might be involved as a checkpoint for cell cycle progression. As the complementation of UV- as well as ionizing radiation-sensitivity is a hallmark of the expression of yeast DNA damage-monitoring checkpoint genes, the ionizing radiation-sensitivity of the immortalized XP-C recipient cell line was tested. Surprisingly, it displayed not only the expected UV-sensitivity (FIG. 1), but also a marked γ-ray sensitivity which is comparable to that of SV40-transformed ataxia telangiectasia cells (FIG. 5). Moreover, this ionizing radiation-sensitivity was significantly complemented by expression of either PCR product no. 3 or no. 4, both of which contain cDNA3 (FIG. 5). Sensitivity to γ-rays is not characteristic of xeroderma pigmentosum cells, as they are defective in nucleotide excision repair. However, the ionizing radiation-sensitivity may result from the chromosomal aberrations which accompanied the immortalization of the particular XP-C cell line.

Most of the radiation protecting RAP-1 4.0 kb mRNA (3510 bp) was isolated as cDNA clones derived from λ-ZAPII human hematopoietic cDNA libraries (FIG. 3). DNA sequencing of both strands has identified a single large open reading frame encoding 648 amino acids bounded by nucleotides 176–2119 and preceded by an upstream in-frame termination codon (FIG. 6). A southern interspecies (Zoo) blot indicated that the RAP-1 gene has been conserved during evolution from mice to man. The RAP-1 mRNA is constitutively transcribed in all of the human tissues examined, albeit at increased amounts in muscle tissues.

The predicted amino acid sequence of the RAP-1 protein as a whole is dissimilar to the sequence of any known protein. However, several regions of RAP-1 display similarity to sub-regions of several known proteins. One such region shows similarity to a sequence shared by several motor/cytoskeleton proteins such as myosin heavy chain, tropomyosin, keratin, lamin, dynein heavy chain, centromeric protein E, as well as to the MAD1 yeast spindle assembly checkpoint gene. This protein motif is likely to represent a region of protein-protein interaction. The essential role of the cytoskeleton and the extracellular matrix in apoptosis makes this homology intriguing (see below).

Is the radiation sensitivity of the immortal XP-C cell line reflected in a necrotic or an apoptotic death? This question was addressed by assaying apoptosis in XP-C cells treated by the γ-radiation mimetic agent etoposide (which causes double stranded breaks because it inhibits topoisomerase II). The kinases inhibitor staurosporine served as a positive control for an apoptosis causing agent. The XP-C etoposide treated cells exhibit nuclear condensation/fragmentation following DAPI staining, the typical oligonucleosomal DNA ladder, and the subdiploid apoptotic peak in single dimension FACS analysis of propidium iodide stained chromosomal DNA. Because cDNA3-transfected immortalized XP-C cells display increased resistance not only to γ-radiation but also to etoposide, it was surmised that cDNA3 expression counters apoptosis induced by DNA damage. This was demonstrated directly by FACS analysis of etoposide treated XP-C cells as compared to similarly treated cDNA3 transfected XP-C cells.

In this context it should be pointed out that the parental XP-C cell line is an SV40 transformed/T antigen producer (Canaani et. al., 1986). The status of p53 or pRb in these cells was not tested. At least one other SV40-transformed human cell line has exhibited radiation induced apoptosis (Jacobson et. al., 1993). It is also noteworthy that while all SV40-immortalized human cell lines tested belong to the same complementation group of immortalization, the XP-C immortal cell line which was generated belongs to a different complementation group (Pereira-Smith and Smith, 1988). This suggests that immortality of that XP-C cell line was achieved, at least in part, by inactivation of a different cell cycle regulator than the one abrogated in most SV40-transformed cells.

The Bcl-2 anti-apoptotic gene responds to different stress signals such as: radiation (UV as well as γ-rays), radiomimetic agents (etoposide, bleomycin sulfate), as well as to a decrease in growth factor supply during serum starvation. It was therefore of interest to test the response of XP-C/XP-C cDNA3 transfectants to apoptosis induced by serum starvation. Importantly, nuclear fragmentation assayed by DAPI staining or FACS analysis clearly showed that RAP-1 cDNA3 also conferred resistance against apoptosis induced by serum starvation (data not shown).

II. Method for gene isolation

The isolation of a checkpoint gene through genetic complementation of mutant human cells lead to the development of a more general method for the isolation of human DNA damage-monitoring checkpoint genes. The experimental approach is based on the generation of radiation-sensitive human cell clones. Their reduced survival to γ-irradiation is dependent on the expression of anti-sense cDNAs selected from a transduced library, resulting in inactivation of specific genes.

For this purpose we have constructed antisense cDNA libraries prepared from untreated and γ-irradiated human cells, built into an EBV-based episomal expression vector. An anti-sense cDNA library can be introduced into human cells while selecting for stable transformants expressing a dominant selectable marker. The primary transformants are replica plated onto polyester circles and the master plates allowed to recover for two days prior to irradiation. The master plates are photographed by an image analyzer and then γ-irradiated at doses sublethal to wild-type human cells. After a week of incubation at 37° C., the irradiated plates are photographed again with an image analyzer under identical conditions. By superimposing the colonies' images before and after irradiation, and comparing their relative sizes by means of the "pattern recognition" software, it is possible to identify those colonies whose growth has been retarded. Transfected cDNA-containing plasmids are isolated from the radiation-sensitive colonies by Hirt extract-transformation of *E. coli*. Secondary transformants are obtained by transduction of isolated plasmids. Analysis of γ-ray sensitive secondary transformants with respect to cell cycle-dependency and progression distinguish those transformants harboring an antisense RNA for a cell cycle progression checkpoint gene from those expressing an antisense RNA for a DNA repair gene.

III. Antisense RNA

Figure 7:
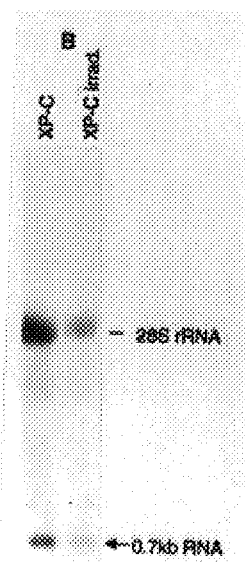
FIG. 7 is a Northern blot which identifies a 0.7 kb antisense RNA to the 4.0 kb RAP-1 mRNA. Hybridization of cDNA3-sense riboprobe to Northern blots of total RNA extracted from SV40-transformed XP-C and UV-irradiated XP-C cells.
Figure 8:
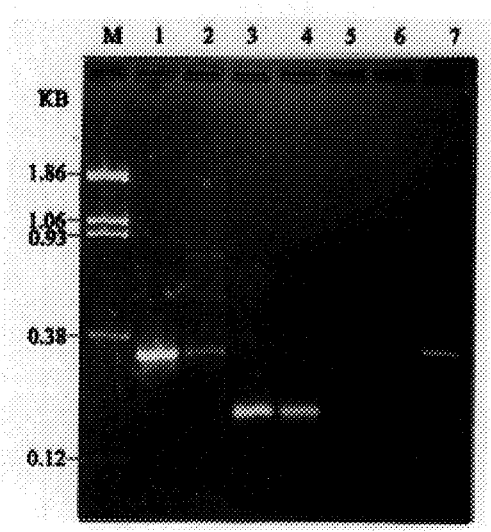
FIG. 8 is an electrophoretic analysis of RT-PCR products from poly(A) selected RNA of SV40-transformed XP-C cells. The RT reactions preceding the PCR were carried out with cDNA3-sense primer 8 (lanes 2,3,5 and 6) and with cDNA3 antisense primer 10 (lane 7), in the presence (lanes 2,3 and 7) or absence (lanes 5 and 6) of reverse transcriptase. The PCR reactions were carried out with cDNA3-sense primer 8 (lanes 1,2,5 and 7), cDNA3-sense primer 62, which is nested to primer 8 (lanes 3,4 and 6), as well as with cDNA3-antisense primer 10 in all seven reactions. The PCR reactions in lanes 1 and 4 were done on a cDNA3 DNA template, and served as markers for the expected products; 322 bp in lane 1, and 183 bp in lane 4. The DNA products in lanes 2 (322 bp) and 3 (183 bp) were extracted from the gel, cloned into a plasmid vector and their nucleotide sequence determined to verify their identity. The sequence of the primers was as follows: Primer 8: 5'-GTCAGGAACTAGGCATGC-3' (complement of nucleotides 322-305 of SEQ. ID. NO: 3). Primer 10: 5'-CCCTGAGGCAAGTCTGGGTACGTA-3' (nucleotides 1-24 of SEQ. ID. NO: 3). Primer 62: 5'-TGGTAGGCAAACTGCAAGG-3' (complement of nucleotides 184-166 of SEQ. ID. NO: 3).

As the possibility of complementation by gene conversion/homologous recombination between a normal copy of cDNA3 and a putative defective segment residing in XP-C cells was ruled out, other possible explanations for the effect of this partial length cDNA on UV-survival were investigated. In an attempt to understand the molecular mechanism of cDNA3 action, a control experiment was carried out in which Northern blots of total XP-C RNA were probed with a cDNA3-sense riboprobe. Surprisingly, the existence of a 0.7 kb long RNA was detected in the non-transfected XP-C cells (FIG. 7). The presence of a naturally occurring antisense RNA to the 4.0 kb mRNA in XP-C cells was verified by the use of cDNA3 specific oligonucleotides as primers in a reverse transcriptase reaction from poly(A)

containing RNA, followed by PCR (FIG. 8). This experiment has shown that the RAP-1 and 0.7 kb RNAs share at least 322 complementary bases, localized to the 3' untranslated region of the former (FIG. 8, lane 2). An RT-PCR experiment with a nested primer gave rise to the expected 183 bp DNA fragment (lane 3). Control tubes lacking the reverse transcriptase did not show any amplification product (lanes 5 and 6), thus eliminating the possibility of either a DNA contamination or a Taq polymerase dependent RT-PCR reaction from the 4.0 kb mRNA. The product of a positive control of RT-PCR from the 4.0 kb mRNA (lane 7) had an identical size (322. bp) to that of the former DNA segment.

These experiments and others have shown that the 4.0 kb and 0.7 kb RNAs share at least 322 complementary bases, localized to the 3' untranslated region of the former (FIGS. 9 and 10 ) (SEQ ID NO: 3).

Although sequences corresponding to fragments of the 0.7 kb RNA have been deposited in a human gene bank (Geneexpress, accession no. Z21914, 265 bp; Takeda et. al., accession no. T10842, 194 bp), these comprise less than half of the 0.7 kb sequence, there is no indication that these fragments are part of a longer sequence, and no indication of their possible function is given. In one case (Takeda, et. al., 1993), the deposited fragment is only one out of a total of 1000 fragments (EST's) isolated from a human pancreatic islet cDNA library!

We hypothesize that the stability/translatability of the 4.0 kb mRNA is repressed by the formation of an RNA duplex with the 0.7 kb antisense RNA (FIG. 11). Transduction followed by transcription of the mRNA encoded by cDNA3 leads through competition for the 0.7 kb RNA to the generation of a cDNA3 mRNA—0.7 kb RNA duplex, while releasing the 4.0 kb mRNA from the duplex (FIG. 11). The latter in turn leads to increased stability/translatability of the 4.0 kb mRNA manifested in increased radioresistance. We propose that the 0.7 kb antisense RNA is a natural repressor of cellular radioresistance.

While the present invention has been described in terms of several preferred embodiments, it is expected that various modifications and improvements will occur to those skilled in the art upon consideration of this disclosure.

The scope of the invention is not to be construed as limited by the illustrative embodiments set forth herein, but is to be determined in accordance with the appended claims.

REFERENCES

Canaani, D., et. al. (1986) Somatic Cell and Mol. Genet. 12, 13–18.
Clarke, A. R. et. al. (1993) Nature 362, 849–852.
Dulic, V., et. al. (1994) Cell 76, 1013–1023.
El-Deiry, W. S., et. al. (1993) Cell 75, 817–825.
Hartwell, L. and Weinert, T. (1989) Science 246, 629–634.
Jacobson, M. D. et. al. (1993) Nature 361, 365–369.
Kastan, M. B., et. al. (1991) Cancer Res. 51, 6304–6311.
Kuerbitz, S. J., et. al. (1992) Proc. Natl. Acad. Sci. USA 89, 7491–7495.
Lowe, S. W. et. al. (1993) Nature 362, 847–849.
Naiman, T. and Canaani, D. (1989) Cancer Genet. and Cytogenet. 40, 65–71.
Pereira-Smith, O. M. and Smith, J. R. (1988) Proc. Natl. Acad. Sci. USA 85, 6042–6046.
Stark, M., et. al. (1989) Biochem. Biophys. Res. Commun. 162, 1351–1356.
Takeda, J., et. al. (1993) Human Mol. Gen. 2, 1793–1798.
Teitz, T., et. al. (1987) Proc. Natl. Acad. Sci. USA 84, 8801–8804.
Teitz, T., et. al. (1990) Gene 87, 295–298.
Yonish-Rouach, E. et. al. (1991) Nature 352, 345–347.

---

I claim:

1. An isolated DNA sequence selected from the group consisting of:
    (i) an isolated DNA sequence encoding a radiation-protecting human checkpoint (RAP-1) protein and comprising the nucleic acid sequence of SEQ. ID. NO: 1; and
    (ii) an isolated DNA sequence encoding a peptide comprising the amino acid sequence of SEQ. ID. NO: 2.

2. An isolated polypeptide comprising the amino acid sequence encoded by the DNA sequence of claim 1.

3. The polypeptide according to claim 2 comprising the amino acid sequence of SEQ. ID. No.: 2.

4. An isolated DNA sequence comprising the nucleic acid sequence of SEQ. ID. No.: 3.

5. An isolated RNA sequence transcribed from the DNA sequence of claim 4.

6. A nucleic acid vector comprising the DNA sequence of claim 1.

7. A nucleic acid vector comprising the DNA sequence of claim 4.

8. The vector according to claim 6 further comprising a promoter sequence controlling expression of said DNA sequence in a host or target cell.

9. The vector according to claim 6 further comprising a promoter sequence controlling expression of said DNA sequence in a host or target cell.

10. A method for the isolation of c-DNA of a DNA damage-monitoring checkpoint gene comprising the steps of:
    (i) transfecting normal cells with an antisense c-DNA library;
    (ii) replica plating said transfected normal cells;
    (iii) γ-irradiating at a sub-lethal dose one of either of the transfected cells or the replicated cells;
    (iv) incubating the γ-irradiated cells and identifying radiation sensitive cells from among the γ-irradiated cells, those cells which do not grow being radiation sensitive; and
    (v) recovering and isolating the c-DNA as an antisense c-DNA from the cells which were not irradiated in step (iii) and which correspond to the cells identified as being radiation sensitive in step (iv).

11. The method of claim 10 further including the step of verifying the identity of the c-DNA as encoding a DNA damage monitoring checkpoint gene by analysis of cell cycle progression.

12. The method of claim 10 wherein the antisense c-DNA is in a plasmid.

13. The method of claim 10 wherein the antisense c-DNA is in a viral vector.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 3509 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Homo sapiens
        ( H ) CELL LINE: ESTABLISHED XERODERMA PIGMENTOSUM GM2096-SV3

( v i i ) IMMEDIATE SOURCE:
        ( B ) CLONE: RAP-1 cDNA ( x i ) SEQUENCE DESCRIPTION: SEQ ID NO:1:

```
TCCAGCGGCG  GCAACGGCGG  CAGCGGCGGC  AGCGGCGGCG  GCTACTGTCT  GGGCTGAGCA      60

GTAGTGCCTC  TCGGGTGGCG  GGTTTCTAGG  CTGCAGGGGC  TTGGTAGGTG  GTGGCAAGGG     120
```

-continued

| | | | | | | |
|---|---|---|---|---|---|---|
| GGCGGCGGCG | GATGCCGGAA | GAGTGCCCGC | CCCGCTTGGC | GGCCCCTGGA | TCGAGATGAG | 180 |
| CGCCTCCGCG | TCGGTCGGGG | GCCCCGTCCC | CCAGCCACCC | CCGGGCCCGG | CCGCTGCTCT | 240 |
| GCCTCCCGGT | TCTGCCGCGC | GGGCCCTGCA | TGTGGAGCTG | CCGTCTCAGC | AGCGGCGTCT | 300 |
| TCGACATCTT | CGGAACATTG | CTGCCCGGAA | CATTGTTAAT | AGAAATGGCC | ATCAGCTCCT | 360 |
| TGATACCTAC | TTTACACTTC | ACTTGTGTAG | TACTGAAAAG | ATATATAAAG | AATTTTATAG | 420 |
| AAGTGAAGTG | ATTAAGAATT | CCTTGAATCC | CACGTGGCGA | AGTCTCGATT | TTGGAATTAT | 480 |
| GCCAGACCGT | CTTGATACAT | CTGTGTCTTG | TTTCGTGGTG | AAGTATGGG | GTGGAAAGGA | 540 |
| GAACATCTAC | CAGCTGTTGA | TTGAATGGAA | AGTCTGTTTG | GATGGGCTGA | AATACTTGGG | 600 |
| TCAGCAGATT | CATGCCCGAA | ACCAAAATGA | GATAATTTTT | GGGCTGAATG | ATGGATACTA | 660 |
| TGGTGCTCCA | TTTGAACATA | AGGGTTATTC | AAATGCTCAG | AAGACTATTC | TTCTGCAGGT | 720 |
| GGATCAGAAC | TGTGTTCGCA | ATTCTTACGA | TGTCTTCTCT | TGCTACGGC | TTCATAGAGC | 780 |
| CCAGTGTGCA | ATTAAACAGA | CTCAGGTAAC | TGTTCAGAAA | ATTGGAAAGG | AAATTGAAGA | 840 |
| AAAACTAAGA | CTCACATCTA | CAAGCAATGA | ACTGAAAAAA | AAAGTGAAT | GCCTGCAGTT | 900 |
| AAAAATTTTG | GTGCTTCAGA | ATGAACTGGA | ACGGCAGAAG | AAAGCTTTGG | GACGGGAGGT | 960 |
| GGCATTACTG | CATAAGCAAC | AAATTGCATT | ACAAGACAAA | GGAAGTGCAT | TTTCAGCTGA | 1020 |
| GCACCTCAAA | CTTCAACTCC | AGAAGGAATC | CCTAAATGAG | CTGAGGAAGG | AGTGCACTGC | 1080 |
| AAAAAGAGAA | CTCTTCTTGA | AGACTAATGC | TCAGTTGACA | ATTCGTTGCA | GGCAGTTACT | 1140 |
| CTCTGAGCTT | TCCTACATTT | ACCCTATTGA | TTTGAATGAA | CATAAGGATT | ACTTTGTATG | 1200 |
| CGGTGTCAAG | TTGCCTAATT | CTGAGGACTT | CCAAGCAAAA | GATGATGGAA | GCATTGCTGT | 1260 |
| TGCCCTTGGT | TATACTGCAC | ATCTGGTCTC | CATGATTTCC | TTTTCCTAC | AAGTGCCCCT | 1320 |
| CAGATATCCT | ATAATTCATA | AGGGGTCTAG | ATCAACAATC | AAAGACAATA | TCAATGACAA | 1380 |
| ACTGACGGAA | AAGGAGAGAG | AGTTTCCACT | GTATCCAAAA | GGAGGGAGA | AGTTGCAGTT | 1440 |
| TGATTATGGT | GTCTATCTTC | TGAACAAAAA | TATAGCACAG | CTAAGATATC | AACATGGACT | 1500 |
| AGGGACTCCA | GACTTGCGGC | AAACCCTTCC | CAACCTGAAA | AACTTCATGG | AGCATGGACT | 1560 |
| AATGGTCAGG | TGTGACAGAC | ATCACACCTC | CAGTGCAATC | CCTGTTCCTA | AGAGACAAAG | 1620 |
| CTCCATATTT | GGGGGTGCAG | ATGTAGGCTT | CTCTGGGGGG | ATCCCTTCAC | CAGACAAAGG | 1680 |
| ACATCGAAAA | CGGGCCAGCT | CTGAGAATGA | GAGACTTCAG | TACAAAACCC | CTCCTCCCAG | 1740 |
| TTACAACTCA | GCATTAGCCC | AGCCTGTGAC | CACCGTCCCC | TCCATGGGAG | AGACCGAGAG | 1800 |
| AAAGATAACA | TCTCTATCCT | CCTCCTTGGA | TACCTCCTTG | GACTTCTCCA | AAGAAAACAA | 1860 |
| GAAAAAGGA | GAGGATCTAG | TTGGCAGCTT | AAACGGAGGC | CACGCGAATG | TGCACCCTAG | 1920 |
| CCAAGAACAA | GGAGAAGCCC | TCTCCGGGCA | CCGGGCCACA | GTCAATGGCA | CTCTCCTACC | 1980 |
| CAGCGAGCAG | GCCGGGTCCG | CCAGTGTCCA | GCTTCCAGGC | GAGTTCCACC | CAGTCTCAGA | 2040 |
| AGCTGAGCTC | TGCTGTACTG | TGGAGCAAGC | AGAAGAAATC | ATCGGGCTGG | AAGCACAGGT | 2100 |
| TTCGCCTCAG | GTGATCAGCT | AGAAGCATTT | AACTGCATCC | CAGTGGACAG | TGCTGTGGCA | 2160 |
| GTAGAGTGTG | ACGAACAAGT | TCTGGGAGAA | TTTGAAGAGT | TCTCCCGAAG | GATCTATGCA | 2220 |
| CTGAATGAAA | ACGTATCCAG | CTTCCGCCGG | CCGCGCAGGA | GTTCCGATAA | GTGAAGTGAG | 2280 |
| CAGGTCAACA | GTAGGACTGG | GGCAGAAGCT | CTGCCTAAAA | TGAAGTGAAA | GCTGCACTTA | 2340 |
| ACCCTTTGTG | ATAATGATGA | CACAAAATGA | ATATTAATGG | AGGATATTCC | TCGGAAAAAC | 2400 |
| AGACTTTGGG | AATGAAGGAG | GGACTCAGGA | TCATTGTTAT | CAGTGGGCCA | AAGTTAGATT | 2460 |
| TTGCTTTCAA | GATTTGCTTT | TCGGGCCTGA | TGATTTTAAA | GCAAAAATCA | CCCTCTAGTT | 2520 |

| | | | | | | |
|---|---|---|---|---|---|---|
| GAAAGAGCTT | ACAGCTCGAG | TCACCTTTTA | GCTATTTGTC | TGCTTTTTAT | TTACCCTTGT | 2580 |
| ATGTTATCCT | CAGAGGGAAG | ATGATAATAT | ATAATAATAT | AATGAACACA | CCCTTAGTTT | 2640 |
| CTCATAACAT | TTGCCCTCAC | CATGGTTTAT | AAAACTTTGG | GAAAACGGAA | TATTCAGAAA | 2700 |
| TAGGTTTCCG | CCATGTACTG | AAAGGTCTGT | GGCCATCTGT | GAGGTAGATG | AAGAAGCAGC | 2760 |
| ATAGTGGTCT | CCTTACATCT | AGGCCTAACT | GTCCCTCTTC | CTGCCCCCGG | GTACCACAGT | 2820 |
| CCACCTTTAG | ACCCTACTGT | CGCCCCATCT | TCTCCGTGGA | TGGGCCATGC | GTTCCTGAAA | 2880 |
| ACAGGACATC | AAGATTCACT | GGTTCTGTAA | CCCAGTAGCT | GTGACGTTCC | ATCTCTTCTA | 2940 |
| ACCAGCCATG | GCCTTCCCCT | CCTCTGCCAT | ACCCTTAATG | CGGCCCTCAG | ATTAGATGAA | 3000 |
| AAACTTGCTC | CTGGTGGATC | CCAAGGGACC | CTCAAGGACC | TCGAGGTTAC | TGCAGTCAGA | 3060 |
| TGCCATCTCA | TCCCTGTGGG | GGCCAAAGTT | TTTATGTGGG | CAGATGCTGT | GGTCAGGAAC | 3120 |
| TAGGCATGCT | TTCTGGCAAT | GCACTCACCA | GACAAAAATC | CTTGATGTAA | ATCCCATGTT | 3180 |
| AATTTATTAA | ATTTAGTCAG | AAGGTCAGCA | TTTACATGAC | AGAATGTATG | TAGAGAGTTG | 3240 |
| GGGTGTCTGG | TAGGCAAACT | GCAAGGCAGT | TGAGATAGTT | GGATTAAGAG | GCTAGACGAG | 3300 |
| ACATAGAATA | CTATTGGTGA | TGTGTGCAAT | TTCATGAATA | TTAAATTATG | TTTCGAAGTC | 3360 |
| CAGTTGTCAT | TCCCGCATTC | AGATTTCATT | TGCTGATGAC | TTTATACGTT | ACGTACCCAA | 3420 |
| GGACATTGCC | TCAGGGTTGC | AAACTCTTTA | AAGGCAAAAT | TTATCCATAT | ATCCATGTAT | 3480 |
| TATATAGAAT | AAAAATTGAA | GTTTACTTC | | | | 3509 |

( 2 ) INFORMATION FOR SEQ ID NO:2:

( i ) SEQUENCE CHARACTERISTICS:
        ( A ) LENGTH: 648 amino acids
        ( B ) TYPE: amino acid
        ( D ) TOPOLOGY: linear ( i i ) MOLECULE TYPE: protein ( i i i ) HYPOTHETICAL: YES ( i v ) ANTI-SENSE: NO ( v i i ) IMMEDIATE SOURCE:
        ( B ) CLONE: RAP-1

( x i ) SEQUENCE DESCRIPTION: SEQ ID NO:2:

```
Met Ser Ala Ser Ala Ser Val Gly Gly Pro Val Pro Gln Pro Pro Pro
 1               5                  10                  15

Gly Pro Ala Ala Ala Leu Pro Pro Gly Ser Ala Ala Arg Ala Leu His
             20                  25                  30

Val Glu Leu Pro Ser Gln Gln Arg Arg Leu Arg His Leu Arg Asn Ile
         35                  40                  45

Ala Ala Arg Asn Ile Val Asn Arg Asn Gly His Gln Leu Leu Asp Thr
     50                  55                  60

Tyr Phe Thr Leu His Leu Cys Ser Thr Glu Lys Ile Tyr Lys Glu Phe
 65                  70                  75                  80

Tyr Arg Ser Glu Val Ile Lys Asn Ser Leu Asn Pro Thr Trp Arg Ser
             85                  90                  95

Leu Asp Phe Gly Ile Met Pro Asp Arg Leu Asp Thr Ser Val Ser Cys
            100                 105                 110

Phe Val Val Lys Ile Trp Gly Gly Lys Glu Asn Ile Tyr Gln Leu Leu
            115                 120                 125

Ile Glu Trp Lys Val Cys Leu Asp Gly Leu Lys Tyr Leu Gly Gln Gln
            130                 135                 140
```

```
Ile His Ala Arg Asn Gln Asn Glu Ile Ile Phe Gly Leu Asn Asp Gly
145                 150                 155                 160

Tyr Tyr Gly Ala Pro Phe Glu His Lys Gly Tyr Ser Asn Ala Gln Lys
                165                 170                 175

Thr Ile Leu Leu Gln Val Asp Gln Asn Cys Val Arg Asn Ser Tyr Asp
            180                 185                 190

Val Phe Ser Leu Leu Arg Leu His Arg Ala Gln Cys Ala Ile Lys Gln
        195                 200                 205

Thr Gln Val Thr Val Gln Lys Ile Gly Lys Glu Ile Glu Glu Lys Leu
    210                 215                 220

Arg Leu Thr Ser Thr Ser Asn Glu Leu Lys Lys Ser Glu Cys Leu
225                 230                 235                 240

Gln Leu Lys Ile Leu Val Leu Gln Asn Glu Leu Glu Arg Gln Lys Lys
                245                 250                 255

Ala Leu Gly Arg Glu Val Ala Leu Leu His Lys Gln Gln Ile Ala Leu
                260                 265                 270

Gln Asp Lys Gly Ser Ala Phe Ser Ala Glu His Leu Lys Leu Gln Leu
            275                 280                 285

Gln Lys Glu Ser Leu Asn Glu Leu Arg Lys Glu Cys Thr Ala Lys Arg
        290                 295                 300

Glu Leu Phe Leu Lys Thr Asn Ala Gln Leu Thr Ile Arg Cys Arg Gln
305                 310                 315                 320

Leu Leu Ser Glu Leu Ser Tyr Ile Tyr Pro Ile Asp Leu Asn Glu His
                325                 330                 335

Lys Asp Tyr Phe Val Cys Gly Val Lys Leu Pro Asn Ser Glu Asp Phe
            340                 345                 350

Gln Ala Lys Asp Asp Gly Ser Ile Ala Val Ala Leu Gly Tyr Thr Ala
        355                 360                 365

His Leu Val Ser Met Ile Ser Phe Phe Leu Gln Val Pro Leu Arg Tyr
370                 375                 380

Pro Ile Ile His Lys Gly Ser Arg Ser Thr Ile Lys Asp Asn Ile Asn
385                 390                 395                 400

Asp Lys Leu Thr Glu Lys Glu Arg Glu Phe Pro Leu Tyr Pro Lys Gly
                405                 410                 415

Gly Glu Lys Leu Gln Phe Asp Tyr Gly Val Tyr Leu Leu Asn Lys Asn
            420                 425                 430

Ile Ala Gln Leu Arg Tyr Gln His Gly Leu Gly Thr Pro Asp Leu Arg
        435                 440                 445

Gln Thr Leu Pro Asn Leu Lys Asn Phe Met Glu His Gly Leu Met Val
    450                 455                 460

Arg Cys Asp Arg His His Thr Ser Ser Ala Ile Pro Val Pro Lys Arg
465                 470                 475                 480

Gln Ser Ser Ile Phe Gly Gly Ala Asp Val Gly Phe Ser Gly Gly Ile
                485                 490                 495

Pro Ser Pro Asp Lys Gly His Arg Lys Arg Ala Ser Ser Glu Asn Glu
            500                 505                 510

Arg Leu Gln Tyr Lys Thr Pro Pro Pro Ser Tyr Asn Ser Ala Leu Ala
        515                 520                 525

Gln Pro Val Thr Thr Val Pro Ser Met Gly Glu Thr Glu Arg Lys Ile
    530                 535                 540

Thr Ser Leu Ser Ser Ser Leu Asp Thr Ser Leu Asp Phe Ser Lys Glu
545                 550                 555                 560

Asn Lys Lys Lys Gly Glu Asp Leu Val Gly Ser Leu Asn Gly Gly His
                565                 570                 575
```

| Ala | Asn | Val | His | Pro | Ser | Gln | Glu | Gln | Gly | Glu | Ala | Leu | Ser | Gly | His |
|---|---|---|---|---|---|---|---|---|---|---|---|---|---|---|---|
| | | | 580 | | | | 585 | | | | | | 590 | | |

| Arg | Ala | Thr | Val | Asn | Gly | Thr | Leu | Leu | Pro | Ser | Glu | Gln | Ala | Gly | Ser |
|---|---|---|---|---|---|---|---|---|---|---|---|---|---|---|---|
| | | 595 | | | | | 600 | | | | | 605 | | | |

| Ala | Ser | Val | Gln | Leu | Pro | Gly | Glu | Phe | His | Pro | Val | Ser | Glu | Ala | Glu |
|---|---|---|---|---|---|---|---|---|---|---|---|---|---|---|---|
| | 610 | | | | | 615 | | | | | 620 | | | | |

| Leu | Cys | Cys | Thr | Val | Glu | Gln | Ala | Glu | Glu | Ile | Ile | Gly | Leu | Glu | Ala |
|---|---|---|---|---|---|---|---|---|---|---|---|---|---|---|---|
| 625 | | | | | 630 | | | | | 635 | | | | | 640 |

| Gln | Val | Ser | Pro | Gln | Val | Ile | Ser |
|---|---|---|---|---|---|---|---|
| | | | | 645 | | | |

(2) INFORMATION FOR SEQ ID NO:3:

(i) SEQUENCE CHARACTERISTICS:
        (A) LENGTH: 322 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: YES (vi) ORIGINAL SOURCE:
        (A) ORGANISM: Homo sapiens
        (H) CELL LINE: GM2096-SV3

(vii) IMMEDIATE SOURCE:
        (B) CLONE: RAP-1 ANTISENSE (xi) SEQUENCE DESCRIPTION: SEQ ID NO:3:

| CCCTGAGGCA | AGTCTGGGTA | CGTAACGTAT | AAAGCAACAG | CAAATGAAAT | CTGAATGCGG | 60 |
|---|---|---|---|---|---|---|
| GAATGACAAC | TGGACTTCGA | AACATAATTT | AATATTCATG | AAATTGCACA | CATACCAATA | 120 |
| GTATTCTATG | TCTCGTCTAG | CCTCTTAATC | CAACTATCTC | AACTGCCTTG | CAGTTTGCCT | 180 |
| ACCAGACACC | CCAACTCTCT | ACATACATTC | TGTCATGTAA | ATGCTGACCT | TCTGACTGAA | 240 |
| ATTTAATAAA | TTAACATGGG | ATTTACATCA | AGGGATTTTT | GTCTGGTGAG | TGCATTGCCA | 300 |
| GAAAGCATGC | CTAGTTCCTG | AC | | | | 322 |